(12) United States Patent
Shirai et al.

(10) Patent No.: US 10,583,043 B2
(45) Date of Patent: Mar. 10, 2020

(54) BACKING HAVING THREE-LAYER STRUCTURE AND AQUEOUS PATCH USING THE BACKING

(75) Inventors: Sadanobu Shirai, Higashikagawa (JP); Masahiro Inazuki, Higashikagawa (JP); Miho Ishigure, Higashikagawa (JP); Hideo Isoda, Otsu (JP); Hiroyuki Sakamoto, Otsu (JP); Takashi Koida, Osaka (JP); Hiroyasu Sakaguchi, Osaka (JP)

(73) Assignees: TEIKOKU SEIYAKU CO., LTD., Kagawa (JP); TOYOBO CO., LTD., Osaka (JP)

( * ) Notice: Subject to any disclaimer, the term of this patent is extended or adjusted under 35 U.S.C. 154(b) by 0 days.

(21) Appl. No.: 13/807,427

(22) PCT Filed: Jul. 11, 2011

(86) PCT No.: PCT/JP2011/065762
§ 371 (c)(1),
(2), (4) Date: Jan. 31, 2013

(87) PCT Pub. No.: WO2012/008395
PCT Pub. Date: Jan. 19, 2012

(65) Prior Publication Data
US 2013/0138057 A1     May 30, 2013

(30) Foreign Application Priority Data

Jul. 12, 2010    (JP) .................................. 2010-157988

(51) Int. Cl.
*A61F 13/02*     (2006.01)
*A61K 31/192*     (2006.01)
(Continued)

(52) U.S. Cl.
CPC ............ *A61F 13/022* (2013.01); *A61K 9/703* (2013.01); *A61K 9/7046* (2013.01);
(Continued)

(58) Field of Classification Search
CPC ... A61F 13/022; A61K 31/167; A61K 31/192; A61K 9/703; A61K 9/7046; A61K 9/7061; B32B 3/266
(Continued)

(56) References Cited

U.S. PATENT DOCUMENTS 5,336,210 A     8/1994   Hidaka et al.
5,462,743 A *   10/1995   Turner .................. A61K 9/703
                                                                                      424/448
(Continued)

FOREIGN PATENT DOCUMENTS

CN          101094662        12/2007
EP           0 484 543         5/1992
(Continued)

OTHER PUBLICATIONS

International Search Report dated Aug. 2, 2011 in International (PCT) Application No. PCT/JP2011/065763.
(Continued)

*Primary Examiner* — Kai H Weng
(74) *Attorney, Agent, or Firm* — Wenderoth, Lind & Ponack, L.L.P.

(57) ABSTRACT

The present invention relates to a backing having a three-layer structure prepared by sticking together an inner fiber layer for holding a pasty preparation, a film layer having through-holes, and an air-permeable outer fiber layer which prevents leaking out of the pasty preparation or a liquid component exuded from the pasty preparation, and also relates to an aqueous patch using the backing which can be applied for a long time.

7 Claims, 9 Drawing Sheets

(51) Int. Cl.
*A61K 31/167* (2006.01)
*A61K 9/70* (2006.01)
*B32B 3/26* (2006.01)

(52) U.S. Cl.
CPC .......... *A61K 9/7061* (2013.01); *A61K 31/167* (2013.01); *A61K 31/192* (2013.01); *B32B 3/266* (2013.01); *Y10T 428/24331* (2015.01)

(58) Field of Classification Search
USPC ....................................................... 604/307
See application file for complete search history.

(56) References Cited

U.S. PATENT DOCUMENTS

| | | | |
|---|---|---|---|
| 5,465,735 A * | 11/1995 | Patel | A61F 13/022 128/888 |
| 5,935,682 A | 8/1999 | Wallström | |
| 6,210,704 B1 | 4/2001 | Sasaki et al. | |
| 6,903,243 B1 | 6/2005 | Burton | |
| 7,078,089 B2 | 7/2006 | Ellis et al. | |
| 2008/0269660 A1 * | 10/2008 | Sigurjonsson et al. | 602/56 |
| 2008/0287027 A1 | 11/2008 | Suzuki et al. | |
| 2010/0076387 A1 * | 3/2010 | Weimann et al. | 604/290 |
| 2013/0164495 A1 | 6/2013 | Isoda et al. | |

FOREIGN PATENT DOCUMENTS

| | | |
|---|---|---|
| JP | 3-161435 | 7/1991 |
| JP | 6-116141 | 4/1994 |
| JP | 6-238784 | 8/1994 |
| JP | 8-217668 | 8/1996 |
| JP | 8-260328 | 10/1996 |
| JP | 9-208469 | 8/1997 |
| JP | 10-298065 | 11/1998 |
| JP | 11-246397 | 9/1999 |
| JP | 2000-143503 | 5/2000 |
| JP | 2003-53894 | 2/2003 |
| JP | 2004-49544 | 2/2004 |
| JP | 2005-314618 | 11/2005 |
| JP | 2007-31322 | 2/2007 |
| WO | 2006/070672 | 7/2006 |
| WO | 2009/082602 A2 | 7/2009 |
| WO | 2012/008396 | 1/2012 |

OTHER PUBLICATIONS

English Translation of International Preliminary Report on Patentability dated Feb. 12, 2013 in International (PCT) Application No. PCT/JP2011/065763.
Office Action dated Feb. 21, 2014 in U.S. Appl. No. 13/809,549.
Search Report dated Nov. 28, 2013 in corresponding European Application No. 11806725.5.
International Search Report dated Aug. 2, 2011 in International (PCT) Application No. PCT/JP2011/065762.
English Translation of International Preliminary Report on Patentability dated Feb. 21, 2013 in International (PCT) Application No. PCT/JP2011/065762.
Machine translation of JP 2000-143503, published May 2000.
Machine translation of JP 8-260328, patented Oct. 1996.
Machine Translation of JP 6-238784, patented Aug. 1994.
Machine translation of JP 2007-031322, published Feb. 2007.
Machine translation of JP 2003-053894, published Feb. 2003.
Machine translation of JP 9-208469, patented Aug. 1997.
English translation of Second Chinese Office Action dated Nov. 15, 2014 in corresponding Chinese Application No. 201180034426.3.
Office Action dated Aug. 14, 2014 in U.S. Appl. No. 13/809,549.
Office Action dated Jul. 10, 2015 in co-pending U.S. Appl. No. 13/809,549.
Office Action dated Dec. 16, 2015 in U.S. Appl. No. 13/809,549.
"Handbook of Synthetic Filament Non-Woven Fabric", pp. 24-27, Revised Edition, Japan Chemical Fibers Association (Jul. 1999), with partial English translation.
Office Action dated Dec. 2, 2016 in related U.S. Appl. No. 13/809,549.
Office Action dated May 10, 2017 in related U.S. Appl. No. 13/809,549.
Office Action dated Aug. 10, 2017 in U.S. Appl. No. 13/809,549.

* cited by examiner (A)

Backing having three-layer structure (B)

Backing having three-layer structure (C)

Aqueous patch

BACKING HAVING THREE-LAYER STRUCTURE AND AQUEOUS PATCH USING THE BACKING

TECHNICAL FIELD

The present invention relates to a backing having a three-layer structure prepared by sticking together an inner fiber layer for holding a pasty preparation, a film layer having through-holes, and an air-permeable outer fiber layer which prevents leaking out of the pasty preparation or a liquid component exuded from the pasty preparation, and also relates to an aqueous patch using the backing which can be applied for a long time.

BACKGROUND ART

Generally, it is considered that an aqueous patch is not suitable to be applied for a long time relative to an oily patch. One of the reasons is the difficulty of controlling the water evaporation in an aqueous patch.

A moisture permeability of an aqueous patch is highly correlated with the properties of a backing. For example, when a woven fabric or a nonwoven fabric is used as a backing, the problem is that its high moisture permeability causes a decrease of the water content in the pasty preparation in a short time and hardens the pasty preparation, resulting in a decrease of the adhesive power. Meanwhile, when a film such as plastic is used as a backing, it can significantly block the water evaporation. However, when it is applied for a long time, a cohesive failure of the pasty preparation often occurs due to sweat, exudate from an affected area or the like, resulting in a decrease of adhesiveness of the patch, a rash caused by dampness and the like.

As a mean to solve the above-mentioned problems, an aqueous patch, which uses a backing having a two-layer structure consisting of a moisture permeable film and a fiber wherein the air permeability of the backing is adjusted, is proposed (Patent Documents 1-3).

However, during the storage of said aqueous patch, a component contained in the pasty preparation such as a fat permeates the film resulting in defects such as a wrinkle, a kink and the like, or the component exudes into the film surface resulting in problems such as stickiness.

Also, regarding a backing prepared by laminating a film and a nonwoven fabric or a woven fabric, an attempt to control the moisture has been made by forming through-holes in the film (Patent Documents 4-5). However, in said backing, a sufficient control of the moisture permeability may not be achieved in some cases depending on the physical properties of the pasty preparation. Namely, a hard pasty preparation containing a fewer amount of liquid components does not sufficiently exude into the woven fabric or the nonwoven fabric, and thus the advantage of the through-holes in the film can not be utilized in some cases. Conversely, when a soft pasty preparation containing a more amount of liquid components is used, the pasty preparation or a liquid component exudes from the woven fabric or the nonwoven fabric and the moisture permeability become out of control, and further, the exudate from the through-holes may cause troubles such as stickiness.

PRIOR ART DOCUMENTS

Patent Documents

Patent Document 1: Japanese Patent Publication A 8-217668

Patent Document 2: Japanese Patent Publication A 10-298065

Patent Document 3: International Publication WO 2006/070672

Patent Document 4: Japanese Patent Publication A 6-116141

Patent Document 5: Japanese Patent Publication A 2000-143503

SUMMARY OF THE INVENTION

Problems to be Solved by the Invention

The object of the present invention is to provide an aqueous patch having an appropriate air permeability, wherein, as a result of the air permeability, the water evaporation from a pasty preparation is adjusted, the adhesive power of the pasty preparation can be maintained for a long time, and the patch can be applied for a long time, shows an excellent drug-release property in a drug-containing patch and a long-time persistence of drug efficacy, and also to provide a backing used in the aqueous patch.

Means for Solving the Problems

The present inventors have studied earnestly in order to solve the above-mentioned problems, discovered that a backing having a three-layer structure prepared by sticking together an inner fiber layer for holding a pasty preparation, a film layer having through-holes, and an air-permeable outer fiber layer which prevents leaking out of the pasty preparation or a liquid component exuded from the pasty preparation can stably control the moisture in the pasty preparation, found that the above-mentioned problems can be solved by the backing, and finally completed the present invention.

Effect of the Invention

An aqueous patch of the present invention having a backing of a three-layer structure, wherein the backing consists of an inner fiber layer for holding a pasty preparation, a film layer having through-holes for controlling the water evaporation, and an air-permeable outer fiber layer which prevents exuding out of the pasty preparation or a liquid component exuded from the pasty preparation and a water-containing pasty preparation is spread on the inner fiber layer side, can appropriately control the water content relative to conventional aqueous patches, and thus can produce the following excellent effects.

The patch can persistently provide a skin with an appropriate moisture.

The patch is excellent in use in that it has a resistance to sweating, less likely to be peeled off even by an exercise during application, and produces no pasty preparation residue on a skin in peeling off after application.

The patch can maintain a therapeutic effect for a long time when a drug is contained in the patch.

Other effects will be apparent from the following description.

BEST MODE FOR CARRYING OUT THE INVENTION

Figure 1:
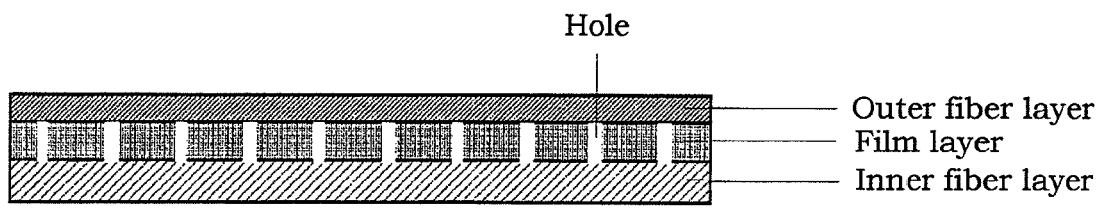
FIG. 1 schematically shows the cross sections of the backing having the three-layer structure and the aqueous patch described in Example 1. (A) and (B) schematically show the cross sections of the backing having the three-layer structure of the present invention. (C) schematically shows the cross section of the aqueous patch of the present invention.
Figure 1:
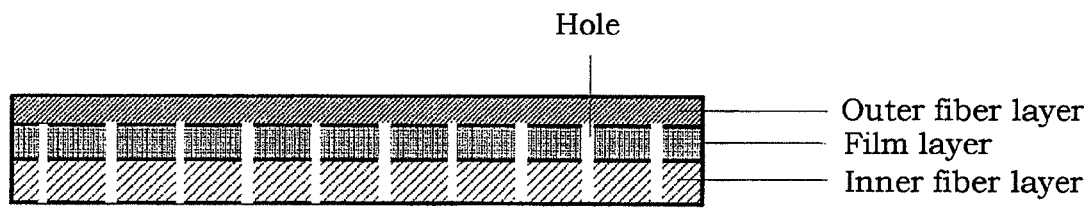
Figure 1:
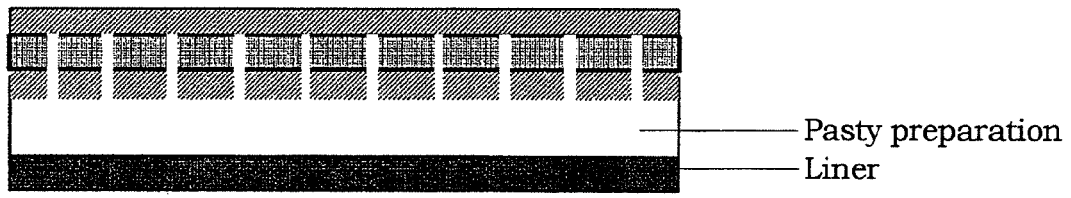

The present invention is presented in the following aspects.

1. A backing for an aqueous patch consisting of three layers, wherein a film layer having through-holes is laminated between an inner fiber layer and an air-permeable outer fiber layer.
2. The backing for an aqueous patch according to the above-mentioned 1, wherein the inner fiber layer is an inner fiber layer having through-holes.
3. The backing for an aqueous patch according to the above-mentioned 1 or 2, wherein the moisture permeability of the backing is 1000-5000 g/m$^2$·24 h.
4. The backing for an aqueous patch according to any one of the above-mentioned 1-3, wherein the opening area of the through-holes per 1 cm$^2$ of the film layer is 1-18 mm$^2$.
5. The backing for an aqueous patch according to any one of the above-mentioned 1-4, wherein the through-hole area per a hole is 0.01-0.8 mm$^2$.
6. An aqueous patch having a backing consisting of three layers, wherein a film layer having through-holes is laminated between an inner fiber layer and an air-permeable outer fiber layer, and a pasty preparation is spread on the inner fiber layer side of the backing.
7. The aqueous patch according to the above-mentioned 6, wherein the inner fiber layer of the backing is an inner fiber layer having through-holes.
8. The aqueous patch according to the above-mentioned 6, wherein the moisture permeability of the backing is 1000-5000 g/m$^2$·24 h.
9. The aqueous patch according to the above-mentioned 6, wherein the opening area of the through-holes of the backing per 1 cm$^2$ of the film layer is 1-18 mm$^2$.
10. The backing for an aqueous patch according to the above-mentioned 6, wherein the opening area of the through-holes of the backing is, the through-hole area per a hole is 0.01-0.8 mm$^2$.
11. The aqueous patch according to the above-mentioned 6, wherein the film layer of the backing is perforated so that 30-90% of the water content in the pasty preparation can remain after incubation at 40° C. for 4 hours.
12. The aqueous patch according to the above-mentioned 6, wherein the pasty preparation contains a drug.
13. The aqueous patch according to the above-mentioned 6, wherein the drug in the pasty preparation is a nonsteroidal antiphlogistic or a local anesthetic.
14. The aqueous patch according to the above-mentioned 6, wherein the drug in the pasty preparation is ketoprofen or felbinac.
15. The aqueous patch according to the above-mentioned 6, wherein the drug in the pasty preparation contains lidocaine.

The backing having the three-layer structure of the present invention can be prepared by sticking the film layer on the outer fiber layer and sticking the inner fiber layer on the film layer by an appropriate adhesive method.

The inner fiber layer is laminated for holding the pasty preparation. The base material used in the inner fiber layer may be a nonwoven fabric or a woven fabric, or may be prepared by directly spraying a fiber component. The material and the basis weight of the inner fiber layer are not limited as long as the inner fiber layer can hold the water-containing pasty preparation, and the material may be, for example, polyethylene, polypropylene, polyester or an olefin elastomer, and the preferred basis weight is 15-80 g/m$^2$.

The film layer is laminated mainly for controlling the water evaporation. The material of the base material used in the film layer can be exemplified by polyethylene, polypropylene or an olefin elastomer, and the thickness is not limited, but 5-50 μm is preferred.

The outer fiber layer is laminated for preventing leaking out of the pasty preparation from the inside or a liquid component exuded from the pasty preparation. The base material used in said fiber layer may be an air-permeable nonwoven fabric or woven fabric, or may be prepared by directly spraying a fiber component. The material is not limited as long as it is an air-permeable fiber component used in a common patch, and can be exemplified by, for example, polyethylene, polypropylene, polyester or an olefin elastomer. Also, the preferred basis weight of the outer fiber layer is 15-80 g/m$^2$.

The perforations in the film layer can be formed by a needle, a laser processing or the like. The perforating process is determined depending on the opening area per 1 cm$^2$ of the film (hereinafter referred to as "opening area"), the number of the through-holes, and the through-hole area per a hole. In case of an olefin elastomer, if the through-holes are opened by a mechanical method such as a needle punch, the opening shape can not be maintained due to the elasticity of the elastomer film and the openings close. Accordingly, a mechanical method is not preferred and thus a hot needle processing is preferred. Because the opening area, the number of the through-holes, and the through-hole area per a hole are the factors which affect the film strength and the flexibility of the backing, they must be adjusted in appropriate ranges.

In the backing having the three-layer structure of the present invention, the opening area per 1 cm$^2$ of the film layer is preferably 1-18 mm$^2$, and more preferably 1-10 mm$^2$. When the opening area is less than 1 mm$^2$, the moisture permeability of the backing becomes too low, the physical properties of the pasty preparation degrade due to the excessive moisture in the pasty preparation, and problems such as a pasty preparation residue on a skin readily occur. Also, when the opening area is greater than 18 mm$^2$, an excessive moisture evaporation occurs, and as a result, the pasty preparation becomes hard, resulting in unfavorable effects such as a decrease of the adhesive power. Meanwhile, as a guide, the number of the through-holes per 1 cm$^2$ is preferably 5-90, and more preferably 10-80. When the number of the through-holes per 1 cm$^2$ is less than 5, the opening area per a hole inevitably becomes large, the moisture unevenly evaporates, and a stable moisture control becomes impossible. Meanwhile, when the number of the through-holes per 1 cm$^2$ is greater than 90, the film strength decreases, and the film is at risk for breakage. Furthermore, the through-hole area per a hole is preferably 0.01-0.8 mm$^2$, more preferably 0.01-0.5 mm$^2$, and still more preferably 0.02-0.18 mm$^2$. When the through-hole area per a hole is less than 0.01 mm$^2$, it is difficult to form uniform through-holes. Conversely, when the through-hole area per a hole is greater than 0.8 mm$^2$, the pasty preparation exudes from the backing.

Additionally, in the backing of the present invention, through-holes may be formed in the inner fiber layer. The backing of the present invention having the through-holes in the inner fiber layer is schematically shown in FIG. 1(B). In this case, the through-holes can be formed by a needle, a laser processing or the like. When the through-holes are formed in both of the film layer and the inner fiber layer, the positions of the through-holes in the film layer and the positions of the through-holes in the inner fiber layer may be or may not be matched.

However, it is preferred that the positions of the through-holes in the inner fiber layer and the positions of the through-holes in the film layer are matched due to the advantage that the perforating process is needed only one time in the manufacturing process of the backing by perforating the inner fiber layer and the film layer together. Furthermore, as a result, when a pasty preparation is laminated on the inner fiber layer side, the pasty preparation can pass through the through-holes of the inner fiber layer, fill the through-holes of the film layer, and reach immediately below the outer fiber layer. Thus, because the pasty preparation fills the through-holes, there is an advantage that the through-holes are not closed by a stretch or contraction of the backing even if the backing stretches or contracts by the motion of the applied site and the moisture can be stably controlled.

The opening area of the inner fiber layer, the number of the through-holes, and the through-hole area per a hole in the inner fiber layer depend on the opening area, the number of the through-holes, and the through-hole area per a hole of the film layer.

The moisture permeability of the backing itself of the present invention is preferably in the range of 1000-5000 g/m$^2$·24 h, and more preferably 2000-4000 g/m$^2$·24 h. When the moisture permeability is less than 1000 g/m$^2$·24 h, the water content in the pasty preparation becomes too high, resulting in a decrease of the pasty preparation strength or adverse effects such as skin irritation caused by dampness etc. When the moisture permeability is greater than 5000 g/m$^2$·24 h, the adhesiveness decreases.

In laminating the three layers of the backing of the present invention, the film layer and the inner fiber layer are stuck together using a heat-seal or an adhesive agent, then perforated, and subsequently, the outer fiber layer is stuck on them using a heat-seal or an adhesive agent, or the film layer is perforated, and then the inner fiber layer and the outer fiber layer are stuck on the film layer using a heat-seal or an adhesive agent. In any case, a through-hole must not be formed in the outer fiber layer.

The pasty preparation which is spread on the backing of the present invention, i.e., the pasty preparation which is laminated on the inner fiber layer side contains water and a water-soluble tackifier as the main ingredients, and if necessary, contains a thickener, a cross-linking agent, a pH regulating agent or the like. A pasty preparation having a sufficient adhesiveness and a shape retention ability is preferred.

Water is a medium for dissolving the adhesive and the thickener, and produces a moisturizing effect by providing a skin with moisture. The amount of water per total pasty preparation amount is preferably 20-70%, and more preferably 30-50%.

The tackifier adjusts the adhesiveness of the pasty preparation, and is selected from water-soluble polymers. The tackifier may be polyacrylic acid, sodium polyacrylate, partially neutralized polyacrylic acid or the like, and they can be used alone or in a combination of two or more of them. The amount of the tackifier per total pasty preparation amount is preferably 3-25%.

The thickener adjusts the shape retention ability of the pasty preparation, and is selected from water-soluble polymers. The thickener may be carboxymethylcellulose sodium, hydroxypropylcellulose, hydroxy methylcellulose or the like, and they can be used alone or in a combination of two or more of them. The amount of the thickener per total pasty preparation amount is preferably 1-20%.

The cross-linking agent further adjusts the adhesiveness and the shape retention ability of the pasty preparation by cross-linking the water-soluble polymers. As the cross-linking agent, a poorly-soluble multivalent metal salt is appropriate, and it may be dihydroxyaluminum aminoacetate, magnesium aluminometasilicate, aluminum hydroxide, synthetic hydrotalcite or the like, and they can be used alone or in a combination of two or more of them. The amount of the cross-linking agent per total pasty preparation amount is preferably 0.01-5%.

If the pasty preparation is strong acid or strong base, there is a risk for excessively damaging a skin during a long-term administration. Accordingly, the appropriate amount of pH regulating agent is contained in the pasty preparation to adjust the pH of the pasty preparation to weak acid, neutral, or weak alkaline.

Also, the aqueous patch of the present invention wherein the pasty preparation is spread on the backing of the present invention is prepared so that the water content after 4 hours incubation at 40° C. in a thermostatic bath becomes preferably 30-90% of the initial amount, more preferably 30-85%, and still more preferably 50-80%.

Furthermore, said pasty preparation may contain a therapeutically effective drug. The drug may be a nonsteroidal anti-inflammatory analgesic, a corticosteroid agent, an antihistamine agent, an anti-itching agent, a hypertensive agent, a local anesthetic, an antifungal agent, an antiepileptic agent, a vasodilator agent, a hormonal agent, a muscle relaxant agent, a stimulating agent, an antivirus agent and the like, and one or more of them can be contained.

In addition, a stabilizing agent, a preservative, a fat, a surfactant or the like may be contained in the pasty preparation if necessary.

The pasty preparation laminated on the backing is covered by a liner. The liner can stably protect the pasty preparation surface, and may be a polyethylene film, a polypropylene film, a polyester film, a processed paper and the like.

The aqueous patch of the present invention is prepared by tucking and spreading the pasty preparation between the inner fiber layer side of the backing having the three-layer structure and the liner. At that time, the thickness of the pasty preparation layer can be adjusted to 300-1500 g/m$^2$. Especially, because the backing of the present invention can show an excellent adhesion stability and a persistent pharmacological effect of a drug even if a relatively thin pasty preparation is spread on the backing, the thickness of the pasty preparation is preferably adjusted to 300-1000 g/m$^2$, and more preferably 300-700 g/m$^2$. Then, the aqueous patch is punched into an appropriate shape depending on the application site, and used as a patch.

EXAMPLES

Although the present invention will be explained with Examples below, the present invention is not intended to be limited to these Examples by any means.

Example (Ex.) 1

To 30 g/m$^2$ of polyethylene nonwoven fabric as the fiber layer was heat-sealed 15 μm of polyethylene film (ethylene-1-octene copolymer), and perforated by a hot needle. Furthermore, 30 g/m$^2$ of polyethylene nonwoven fabric as the outer fiber layer was partially stuck by an adhesive agent on the film surface opposite to the inner fiber layer to obtain a backing having a three-layer structure with 16 holes/cm$^2$, the hole area of 0.13 mm$^2$/hole, and the opening area of 2.5 mm$^2$/cm$^2$.

The moisture permeability of this backing was measured according to the method described in the Japanese Industrial Standards (Jis) L1099. The moisture permeability of this backing was 994 g/m$^2$·24 h.

Then, to 400.2 g of glycerin were added 40 g of partially neutralized polyacrylic acid, 40 g of carboxymethylcellulose sodium, 3 g of hydroxypropylcellulose, 3 g of castor oil, 1 g of polyoxyethylene sorbitan monolaurate and 0.6 g of dihydroxyaluminum aminoacetate, and dispersed (polymer dispersion). To 435 g of purified water were added 50 g of polyacrylic acid, 5 g of tartaric acid and 0.7 g of disodium edetate and mixed, and to the obtained solution was added a solution of 1 g of methylparaben and 0.5 g of propylparaben in 20 g of propylene glycol, and mixed. To this mixed solution was slowly added the previously prepared polymer dispersion with stirring, and stirred until the mixture became homogeneous to prepare a pasty preparation.

This pasty preparation was tucked and spread between the inner fiber layer side of the backing having the three-layer structure and polypropylene film (50 μm) as the liner so that the weight became about 500 g/m$^2$, and punched into the size of 10 cm×14 cm to obtain a desired aqueous patch. The obtained patch was sealed in a packaging bag, and stored at room temperature.

Examples 2-8

The backing having the three-layer structure, in which the hole area and the opening area were adjusted by a perforating process using a hot needle, was prepared, and the moisture permeability of each backing was measured.

The hole area, the opening area, and the measured moisture permeability of each backing are shown in Table 1.

Furthermore, using each backing, the pasty preparation prepared in the same way as Example 1 was spread on the backing to prepare the aqueous patch of each Example. Each obtained patch was sealed in a packaging bag, and stored at room temperature.

Comparative Example (Comp.) 1

Using a polyester nonwoven fabric (basis weight: 100 g/m$^2$) as the backing, the pasty preparation prepared in the same way as Example 1 was spread on the backing to prepare the patch of Comparative Example 1. The obtained patch was sealed in a packaging bag, and stored at room temperature.

Comparative Example 2

To a nonwoven fabric consisting of 60% of rayon, 28% of polyethylene, and 12% of polypropylene was heat-sealed ethylenemethyl methacrylate so that the thickness became 15 μm to prepare a backing.

The moisture permeability of this backing is shown in Table 1.

Using this backing, the pasty preparation prepared in the same way as Example 1 was spread on the backing to prepare the aqueous patch of Comparative Example 2. The obtained patch was sealed in a packaging bag, and stored at room temperature.

Comparative Example 3

To polyethylene was mixed 50% of calcium carbonate, and stretched so that the thickness became 40 μm to prepare a microporous membrane film. To this film was stuck a 45 g/m$^2$ of polyethylene nonwoven fabric to prepare the backing of Comparative Example 3.

The moisture permeability of this backing is shown in Table 1.

Using this backing, the pasty preparation prepared in the same way as Example 1 was spread on the backing to prepare the aqueous patch of Comparative Example 3. The obtained patch was sealed in a packaging bag, and stored at room temperature.

This backing was prepared in reference to the description of Patent Document 5.

Test Example I-1. Measurement of Water Content in Patch

Figure 2:
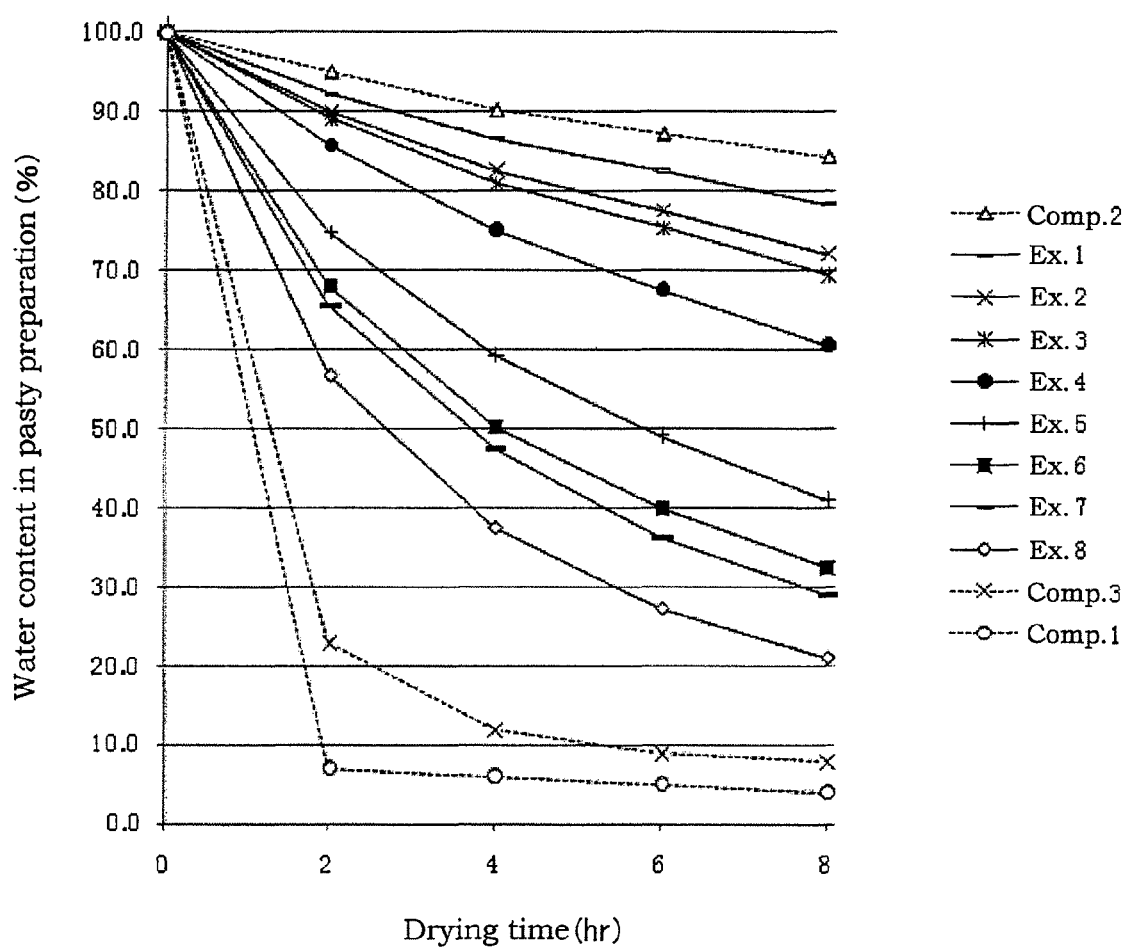
FIG. 2 shows the change of the water content of each formulation of Test Example I-1.

Each patch of Examples 1-8 and Comparative Examples 1-3 was stored in a dry condition at 40° C., and the weight of each patch was measured with time and converted to the decreased amount of water to obtain the change of the water content in the pasty preparation. The results are shown in FIG. 2. In the Figure, the initial water content is set to 100%, and the water content is shown in % of the initial value. Also, the value of the water content in the pasty preparation after dried for 4 hours is shown in Table 1.

Test Example I-2. Adhesive Power Test of Patch

Regarding each patch of Examples 4, 5 and 7 and Comparative Examples 1 and 3, the adhesive power was measured according to the method described in Japanese Industrial Standards (JIS) Z0237.

Also, the above-mentioned formulations were each stored in a dry condition at 40° C. and the change of the adhesive power was determined with time. The test results are shown in Table 2. The adhesive power in the Table is shown in the weight (g) of a steel ball which stopped on the pasty preparation surface. Furthermore, the value in parentheses is the water content in the pasty preparation of each formulation after dried for 4 hours at 40° C. (% of the initial value).

TABLE 1

| | Hole area (mm²) | Opening area (mm²/cm²) | Moisture permeability of backing (g/m² · 24 hr) | Water content in pasty preparation after dried for 4 hours at 40° C. (% of the initial value) |
|---|---|---|---|---|
| Ex. 1 | 0.131 | 2.5 | 944 | 86.6 |
| Ex. 2 | 0.330 | 6.2 | 1540 | 82.6 |
| Ex. 3 | 0.157 | 5.9 | 1695 | 81.0 |
| Ex. 4 | 0.106 | 2.0 | 2610 | 75.1 |
| Ex. 5 | 0.099 | 3.7 | 3681 | 59.4 |
| Ex. 6 | 0.070 | 2.1 | 4000 | 50.3 |
| Ex. 7 | 0.081 | 2.4 | 4475 | 47.4 |
| Ex. 8 | 0.061 | 2.7 | 4903 | 37.4 |
| Comp. 1 | — | — | — | 6.0 |
| Comp. 2 | — | — | 224 | 90.2 |
| Comp. 3 | — | — | 4500 | 11.8 |

TABLE 2

| Drying time | 0 hr | 2 hr | 4 hr | 8 hr  n = 3 |
|---|---|---|---|---|
| Ex. 4 (75.1%) | 28 g | 28 g | 28 g | 22 g |
| Ex. 5 (59.4%) | 28 g | 28 g | 28 g | 22 g |
| Ex. 7 (47.4%) | 28 g | 28 g | 16 g | 16 g |
| Comp. 1 (6.0%) | 16 g | 4 g | 4 g | 4 g |
| Comp. 3 (11.8%) | 28 g | 6 g | 2 g | 2 g |

Test Example 1-3. Applicability Evaluation Test of Patch

The test formulation of each patch of Examples 4 and 5 and Comparative Examples 1 and 2 was applied to three healthy adult males for 24 hours to evaluate the applicability of each patch. The results are shown in Table 3.

TABLE 3

| Subject | Subject 1 | Subject 2 | Subject 3 |
|---|---|---|---|
| Ex. 4 | No peeling during the application and no pasty preparation residue on the skin in peeling were observed. | No peeling during the application and no pasty preparation residue on the skin in peeling was observed. | The circumference of the patch slightly peeled about 15 hours after the application. No pasty preparation residue on the skin in peeling was observed. |
| Ex. 5 | No peeling during the application and no pasty preparation residue on the skin in peeling were observed. | No peeling during the application and no pasty preparation residue on the skin in peeling were observed. | The circumference of the patch slightly peeled about 20 hours after the application. About 5% of the pasty preparation remained on the skin in peeling. |
| Comp. 1 | The patch completely peeled about 9 hours after the application. | The patch completely peeled about 13 hours after the application. | About 50% of the patch peeled 24 hours after the application. The pasty preparation extremely adhered to the skin in peeling and pain occurred. |
| Comp. 2 | No peeling was observed during the application. About 10% of the pasty preparation remained on the skin in peeling. | The patch completely peeled about 17 hours after the application. | The pasty preparation significantly swelled and slippage of the backing occurred about 15 hours after the application. About 30 % of the pasty preparation remained on the skin in peeling. |

[Discussion]

As shown in Table 2, all patches of Examples maintained excellent adhesive powers. It can be considered that this result was caused from the small change in adhesiveness of the pasty preparation due to the gradual and stable water evaporation from the pasty preparation of each patch of Examples as shown in FIG. 2.

Meanwhile, the adhesive powers of both patches of Comparative Examples 1 and 3 significantly decreased. It is considered that this result about these formulations of Comparative Examples was caused from the rapid water evaporation from the pasty preparation resulting in phenomena such as semi-solidification of the water-soluble polymers dissolved in the pasty preparation.

Also, the result of the applicability test shown in Table 3 demonstrated that the patches of Examples were much more excellent in applicability than the patches of Comparative Examples. Namely, while each patch of Examples of the present invention caused almost no peeling of the formulation and almost no pasty preparation residue in peeling after 24 hours application, each patch of Comparative Examples 1 and 2 caused a significant peeling of the formulation from the skin and was proved to be inappropriate for 24 hours application in some cases. Especially, regarding the formulation of Comparative Example 1, some Subjects complained about pain in peeling and a large change in the physical properties of the pasty preparation due to the rapid water evaporation during the application was observed. Also, the significant pasty preparation residue in peeling about the patch of Comparative Example 2 proved that the backing of the patch of Comparative Example 2 could not sufficiently control the moisture of the pasty preparation and resulted in a significant degradation of the physical properties of the pasty preparation.

Example 9

To 30 g/m² of polyethylene nonwoven fabric as the inner fiber layer was heat-sealed 20 μm of polyethylene film (ethylene-1-octene copolymer), and perforated by a hot needle. Furthermore, 50 g/m² of polyethylene nonwoven fabric as the outer fiber layer was partially stuck by an adhesive agent on the film surface opposite to the inner fiber layer to obtain a backing having a three-layer structure with 32 holes/cm², the average hole area of 0.099 mm²/hole, and the opening area of 3.7 mm²/cm². The moisture permeability of this backing was 3700 g/m²·24 h.

Then, a pasty preparation was prepared. To 390 g of glycerin were added 40 g of partially neutralized polyacrylic acid, 40 g of carboxymethylcellulose sodium, 2.5 g of hydroxypropylcellulose and 0.7 g of dihydroxyaluminum aminoacetate, and dispersed (polymer dispersion).

To a mixed solution of 436.7 g of purified water, 50 g of polyacrylic acid, 50 g of tartaric acid and 0.6 g of disodium edetate were added a solution of 3 g of ketoprofen dissolved in a mixture of 5 g of crotamiton, 5 g of diisopropanolamine, 5 g of N-methyl-2-pyrrolidone and 5 g of purified water, and a solution of 1 g of methylparaben and 0.5 g of propylparaben dissolved in 10 g of propylene glycol, and mixed.

To this mixture was slowly added the previously prepared dispersion with stirring, and stirred until the mixture became homogeneous to prepare a pasty preparation.

This pasty preparation was tucked and spread between the inner fiber layer side of the backing having the three-layer structure and 50 μm of polypropylene film so that the weight became about 300 g/m$^2$, and punched into the size of 10 cm×14 cm to obtain the patch of Example 9. The obtained patch was sealed in a packaging bag, and stored at room temperature.

Examples 10-18

According to the pasty preparation composition shown in Table 4, each patch of Examples was prepared in the same method as Example 9.

Test Example II-1. Water Content Measurement Test of Patch

Figure 3:
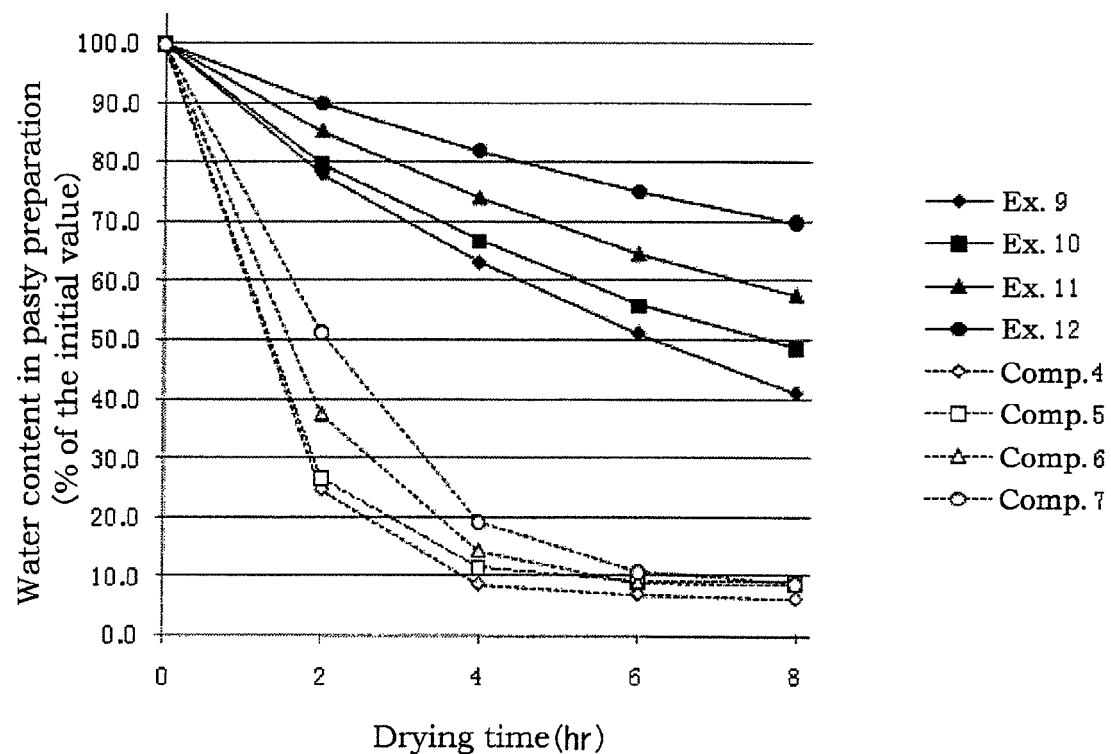
FIG. 3 shows the change of the water content of each formulation of Test Example II-1.

Each patch of Examples 9-12 and Comparative Examples 4-7 was stored in a dry condition at 40° C., and the weight of each patch was measured with time and converted to the decreased amount of water to obtain the change of the water content in the pasty preparation. The results are shown in FIG. 3. In the Figure, the initial water content is set to 100%, and the water content is shown in % of the initial value.

Test Example II-2A. Adhesive Power Test of Patch

Regarding each patch of Examples 9-12 and Comparative Examples 4-7, the adhesive power was measured according to the method described in Japanese Industrial Standards (JIS) Z0237. Also, each patch was stored in a dry condition at 40° C. and the change of the adhesive power was determined with time. The test results are shown in Table 6. The adhesive power in the Table is shown in the weight (g) of a steel ball which stopped on the pasty preparation surface. Furthermore, the value in parentheses is the water content in the pasty preparation of each formulation after dried for 4 hours at 40° C. (% of the initial value).

TABLE 4

|  | Ex. 9 | Ex. 10 | Ex. 11 | Ex. 12 | Ex. 13 | Ex. 14 | Ex. 15 | Ex. 16 | Ex. 17 | Ex. 18 |
| --- | --- | --- | --- | --- | --- | --- | --- | --- | --- | --- |
| Partially neutralized polyacrylic acid | 4 | 4 | 4 | 4 | 4 | 4 | 4 | 4 | 4 | 4 |
| Polyacrylic acid | 5 | 5 | 5 | 5 | 5 | 5 | 5 | 5 | 4 | 4 |
| Carboxymethylcellulose sodium | 4 | 4 | 4 | 4 | 4 | 4 | 4 | 4 | 4 | 4 |
| Hydroxypropylcellulose | 0.25 | 0.25 | 0.25 | 0.25 | 0.25 | 0.25 | 0.25 | 0.25 | 0.25 | 0.25 |
| Glycerin | 39 | 39 | 39 | 39 | 33.17 | 33.17 | 33.17 | 33.17 | 14.16 | 14.16 |
| Propylene glycol | 1 | 1 | 1 | 1 | 1 | 1 | 1 | 1 | 1 | 1 |
| Sorbitol |  |  |  |  | 20 | 20 |  |  |  |  |
| Crotamiton | 0.5 | 0.5 | 0.5 | 0.5 | 0.5 | 0.5 | 0.5 | 0.5 | 0.5 | 0.5 |
| Diisopropanolamine | 0.5 | 0.5 | 0.5 | 0.5 | 0.5 | 0.5 | 0.5 | 0.5 | 0.5 | 0.5 |
| N-Methyl-2-pyrrolidone | 0.5 | 0.5 | 0.5 | 0.5 | 0.5 | 0.5 | 0.5 | 0.5 | 0.5 | 0.5 |
| Tartaric acid | 0.5 | 0.5 | 0.5 | 0.5 | 0.5 | 0.5 | 0.5 | 0.5 | 0.5 | 0.5 |
| Disodium edetate | 0.06 | 0.06 | 0.06 | 0.06 | 0.06 | 0.06 | 0.06 | 0.06 | 0.06 | 0.06 |
| Dihydroxyaluminum aminoacetate | 0.07 | 0.07 | 0.07 | 0.07 | 0.07 | 0.07 | 0.07 | 0.07 | 0.08 | 0.08 |
| Methylparaben | 0.1 | 0.1 | 0.1 | 0.1 | 0.1 | 0.1 | 0.1 | 0.1 | 0.1 | 0.1 |
| Propylparaben | 0.05 | 0.05 | 0.05 | 0.05 | 0.05 | 0.05 | 0.05 | 0.05 | 0.05 | 0.05 |
| Purified water | 44.17 | 44.17 | 44.17 | 44.17 | 30.0 | 30.0 | 50.0 | 50.0 | 70.0 | 70.0 |
| Ketoprofen | 0.3 | 0.3 | 0.3 | 0.3 | 0.3 | 0.3 | 0.3 | 0.3 | 0.3 | 0.3 |
| Total | 100 | 100 | 100 | 100 | 100 | 100 | 100 | 100 | 100 | 100 |
| Pasty preparation weight (g/m$^2$) | 300 | 500 | 700 | 1000 | 500 | 1000 | 500 | 1000 | 500 | 1000 |
| Water content (%) | — | — | — | — | 30.0 | 30.0 | 50.0 | 50.0 | 70.0 | 70.0 |

Comparative Examples 4-7

Using a polyester nonwoven fabric (basis weight: 100 g/m$^2$) as the backing, each patch of Comparative Examples was prepared in the same method as Example 9 according to the pasty preparation composition shown in Table 5.

TABLE 5

|  | Comp. 4 | Comp. 5 | Comp. 6 | Comp. 7 |
| --- | --- | --- | --- | --- |
| Partially neutralized polyacrylic acid | 4 | 4 | 4 | 4 |
| Polyacrylic acid | 5 | 5 | 5 | 5 |
| Carboxymethylcellulose sodium | 4 | 4 | 4 | 4 |
| Hydroxypropylcellulose | 0.25 | 0.25 | 0.25 | 0.25 |
| Glycerin | 39 | 39 | 39 | 39 |
| Propylene glycol | 1 | 1 | 1 | 1 |
| Sorbitol |  |  |  |  |
| Crotamiton | 0.5 | 0.5 | 0.5 | 0.5 |
| Diisopropanolamine | 0.5 | 0.5 | 0.5 | 0.5 |
| N-Methyl-2-pyrrolidone | 0.5 | 0.5 | 0.5 | 0.5 |
| Tartaric acid | 0.5 | 0.5 | 0.5 | 0.5 |
| Disodium edetate | 0.06 | 0.06 | 0.06 | 0.06 |
| Dihydroxyaluminum aminoacetate | 0.07 | 0.07 | 0.07 | 0.07 |
| Methylparaben | 0.1 | 0.1 | 0.1 | 0.1 |
| Purified water | 44.17 | 44.17 | 44.17 | 44.17 |
| Ketoprofen | 0.3 | 0.3 | 0.3 | 0.3 |
| Total | 100 | 100 | 100 | 100 |
| Pasty preparation weight (g/m$^2$) | 300 | 500 | 700 | 1000 |
| Water content (%) | — | — | — | — |

TABLE 6 n = 3

| Drying time | 0 hr | 2 hr | 4 hr | 8 hr |
| --- | --- | --- | --- | --- |
| Ex. 9 (63.1%) | 16 g | 16 g | 12 g | 12 g |
| Ex. 10 (66.8%) | 16 g | 16 g | 16 g | 12 g |
| Ex. 11 (74.1%) | 22 g | 22 g | 22 g | 16 g |
| Ex. 12 (81.9%) | 28 g | 28 g | 22 g | 22 g |
| Comp. 4 (8.7%) | 12 g | 4 g | 2 g | 2 g |
| Comp. 5 (11.5%) | 12 g | 4 g | 2 g | 2 g |
| Comp. 6 (14.5%) | 16 g | 8 g | 6 g | 6 g |
| Comp. 7 (19.2%) | 22 g | 12 g | 8 g | 8 g |

Test Example II-2B. Adhesive Power Test of Patch

Regarding each patch of Examples 13-18, the adhesive power was measured according to the method described in Japanese Industrial Standards (JIS) Z0237. Also, each patch was stored in a dry condition at 40° C. and the change of the adhesive power was determined with time. The results are shown in Table 7. The adhesive power in the Table is shown in the weight (g) of a steel ball which stopped on the pasty preparation surface. Furthermore, the value in parentheses is the water content in the pasty preparation of each formulation after dried for 4 hours at 40° C. (% of the initial value).

TABLE 7

| Drying time | 0 hr | 2 hr | 4 hr | 8 hr n = 3 |
|---|---|---|---|---|
| Ex. 13 (78.7%) | 22 g | 22 g | 22 g | 22 g |
| Ex. 14 (87.4%) | 45 g | 45 g | 36 g | 36 g |
| Ex. 15 (66.9%) | 28 g | 28 g | 22 g | 22 g |
| Ex. 16 (80.4%) | 45 g | 45 g | 45 g | 36 g |
| Ex. 17 (55.4%) | 28 g | 28 g | 16 g | 16 g |
| Ex. 18 (73.1%) | 45 g | 45 g | 36 g | 36 g |

Test Example II-3. In Vitro Excised Skin Permeability Test of Ketoprofen-Containing Patch in Hairless Rat Each patch of Examples 10 and 12 and Comparative Examples 5 and 7 was punched into a round shape of 14 mm in diameter to obtain the test formulation.

An excised skin of a hairless rat was set on a Franz diffusion cell, and each test formulation was applied in the upper part of the excised skin. The receptor was filled with phosphate buffer, the receptor solution was sampled with time, and the amount of ketoprofen in the sample solution was measured and converted into the amount which permeated the excised skin. The results are shown in FIG. 4.

[Discussion]
i) Adhesiveness
(1) Thickness and Adhesive Power of Pasty Preparation
As shown in the result of Table 6, the patches of Examples were more excellent in adhesiveness than the patches of Comparative Examples in all pasty preparation thicknesses. Especially, while the formulations of Comparative Examples having the pasty preparation thickness of 500 g/m² or less showed almost no adhesive power after dried for 8 hours, the formulations of Examples having the pasty preparation thickness of 300 g/m² showed the same or more excellent adhesive power than the formulation of Comparative Example having the thickness of 1000 g/m².

Figure 4:
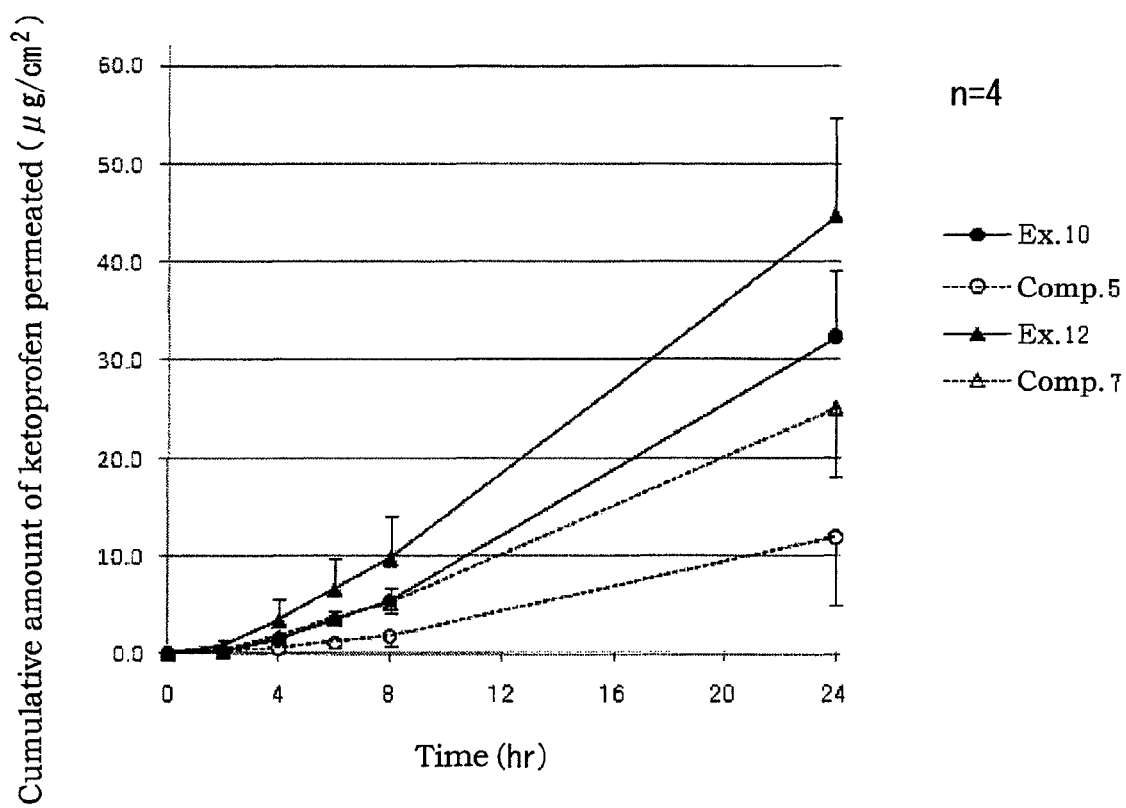
FIG. 4 shows the result of in vitro skin permeability test of each formulation of Test Example II-3.

(2) Water Content and Adhesive Power of Pasty Preparation
As shown in Table 7, all formulations of Examples were proved to show excellent adhesiveness. Especially, formulations of Examples 13-16 having the relatively low water content (initial water content: 30% or 50%) were proved to be excellent in adhesion stability.

ii) Drug-Release Property
As shown in FIG. 4, each formulation of Examples showed the more excellent ketoprofen-release property than each formulation of Comparative Examples. Especially, when the patch of Example was compared to the patch of Comparative Example having the same pasty preparation thickness (cumulative amount of drug permeated after 24 hours from the start of the test about the patch of Example/cumulative amount of drug permeated after 24 hours from the start of the test about the patch of Comparative Example), the comparison between the thin formulations (500 g/m²) showed the 2.7 times higher permeability and the comparison between the thick formulations (1000 g/m²) showed the 1.8 times higher permeability in the patch of Example than the patch of Comparative Example. Namely, it was found that the formulation of Example showed the higher drug-release property than the formulation of Comparative Example especially in the comparison between the thin formulations.

Examples 19 and 20

Each aqueous patch of Examples was prepared in the same method as Example 9 according to the formula shown in Table 8.

Comparative Examples 8 and 9

Using a polyester nonwoven fabric (basis weight: 115 g/m²) as the backing, each aqueous patch of Comparative Examples was prepared in the same method as Example 8 according to the formula shown in Table 8.

TABLE 8

|  | Ex. 19 | Ex. 20 | Comp. 8 | Comp. 9 |
|---|---|---|---|---|
| Partially cross-linked polyacrylic acid | 2 | 2 | 2 | 2 |
| Partially neutralized polyacrylic acid | 1.5 | 1.5 | 1.5 | 1.5 |
| Glycerin | 15 | 15 | 15 | 15 |
| Propylene glycol | 3.0 | 3.0 | 3.0 | 3.0 |
| Sorbitol | 21.5 | 21.5 | 21.5 | 21.5 |
| Crotamiton | 0.5 | 0.5 | 0.5 | 0.5 |
| Diisopropanolamine | 3.0 | 3.0 | 3.0 | 3.0 |
| Tartaric acid | 0.2 | 0.2 | 0.2 | 0.2 |
| Disodium edetate | 0.1 | 0.1 | 0.1 | 0.1 |
| Magnesium aluminometasilicate | 1.0 | 1.0 | 1.0 | 1.0 |
| Methylparaben | 0.1 | 0.1 | 0.1 | 0.1 |
| Propylparaben | 0.05 | 0.05 | 0.05 | 0.05 |
| Purified water | 51.55 | 51.55 | 51.55 | 51.55 |
| Felbinac | 0.5 | 0.5 | 0.5 | 0.5 |
| Total | 100 | 100 | 100 | 100 |
| Pasty preparation weight (g/m²) | 500 | 1000 | 500 | 1000 |
| Water content (%) | — | — | — | — |

Test Example III. Excised Skin Permeability Test of Felbinac-Containing Patch

Each patch of Examples 19 and 20 and Comparative Examples 8 and 9 was punched into a round shape of 14 mm in diameter, subjected to the same test as Test Example II-3, and the felbinac-release property from each formulation was investigated. The results are shown in FIG. 5.

Figure 5:
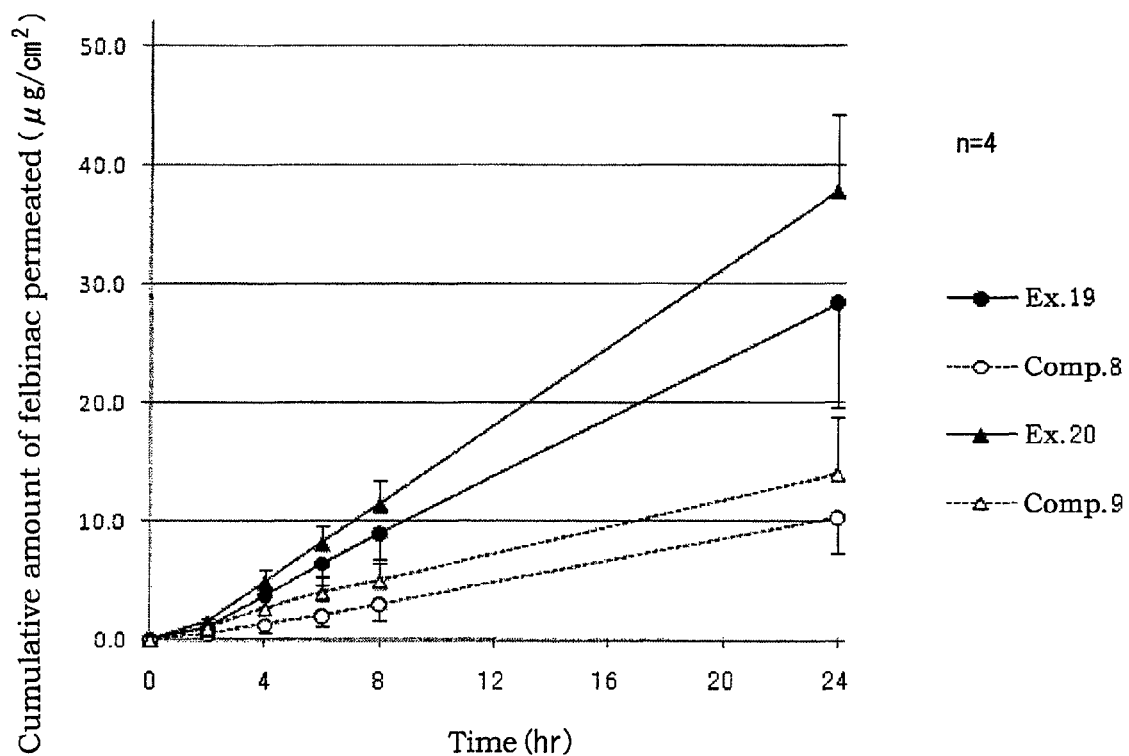
FIG. 5 shows the result of in vitro skin permeability test of each formulation of Test Example III.

[Discussion]
Drug-Release Property
As shown in FIG. 5, the formulations of Examples showed the more excellent felbinac-release properties than the formulations of Comparative Examples. When the patch of Example was compared to the patch of Comparative Example in the drug-release amount (cumulative amount of drug permeated after 24 hours from the start of the test about the patch of Example/cumulative amount of drug permeated after 24 hours from the start of the test about the patch of Comparative Example), the formulations of Examples showed about 2.7 times higher release properties than the formulations of Comparative Examples in the comparison between the thin formulations (500 g/m²) and the comparison between the thick formulations (1000 g/m²), and thus were proved to be excellent formulations in felbinac-release property.

Examples 21-23

Each aqueous patch of Examples was prepared in the same method as Example 9 according to the formula shown in Table 9.

Comparative Examples 11-13

Using a polyester nonwoven fabric (basis weight: 125 g/m²) as the backing, each aqueous patch of Comparative Examples was prepared in the same method as Example 9 according to the formula shown in Table 9.

TABLE 9

|  | Ex. 21 | Ex. 22 | Ex. 23 | Comp. 10 | Comp. 11 | Comp. 12 |
|---|---|---|---|---|---|---|
| Polyacrylic acid | 2 | 2 | 2 | 2 | 2 | 2 |
| Sodium polyacrylate | 5 | 5 | 5 | 5 | 5 | 5 |
| Carboxy-methylcellulose sodium | 5 | 5 | 5 | 5 | 5 | 5 |
| Polyvinyl alcohol | 0.5 | 0.5 | 0.5 | 0.5 | 0.5 | 0.5 |
| Glycerin | 18 | 18 | 18 | 18 | 18 | 18 |
| Propylene glycol | 5 | 5 | 5 | 5 | 5 | 5 |
| Sorbitol | 19 | 19 | 19 | 19 | 19 | 19 |
| Tartaric acid | 1.5 | 1.5 | 1.5 | 1.5 | 1.5 | 1.5 |
| Disodium edetate | 0.1 | 0.1 | 0.1 | 0.1 | 0.1 | 0.1 |
| Aluminum hydroxide | 0.3 | 0.3 | 0.3 | 0.3 | 0.3 | 0.3 |
| Purified water | 38.6 | 38.6 | 38.6 | 38.6 | 38.6 | 38.6 |
| Lidocaine | 5 | 5 | 5 | 5 | 5 | 5 |
| Total | 100 | 100 | 100 | 100 | 100 | 100 |
| Pasty preparation weight (g/m²) | 500 | 1000 | 300 | 500 | 1000 | 300 |
| Water content (%) | — | — | — | — | — | — |

Test Example IV-1. Water Content Measurement Test of Patch

Figure 6:
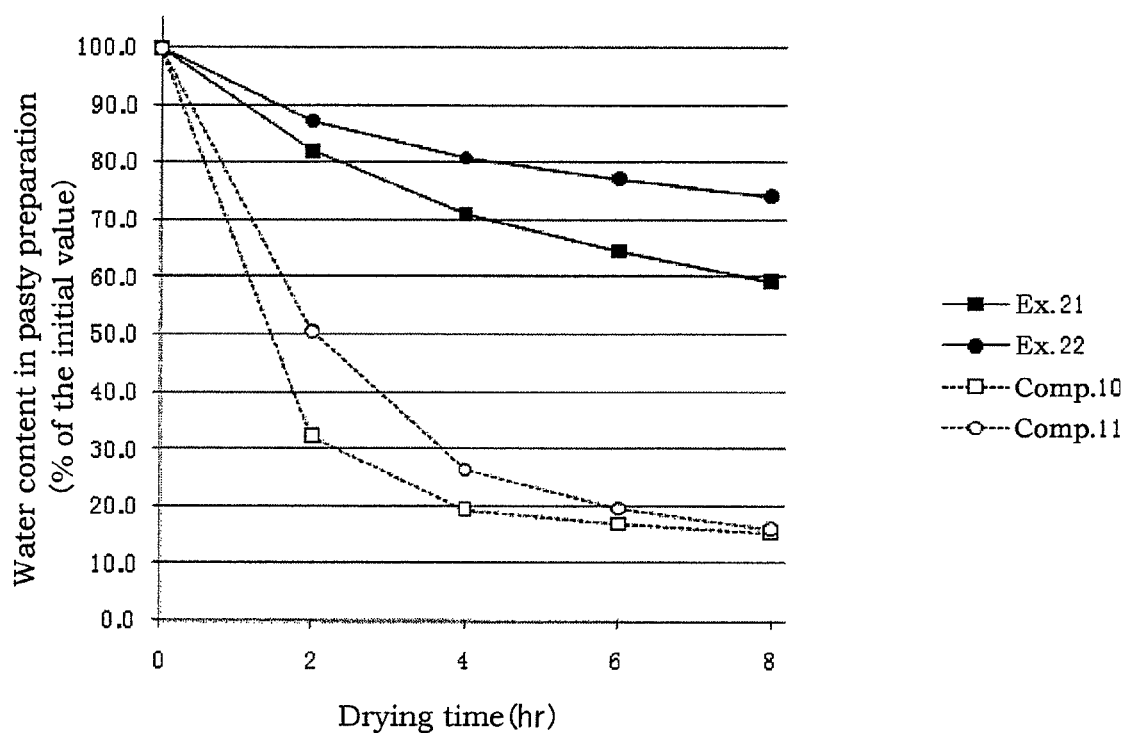
FIG. 6 shows the change of the water content of each formulation of Test Example IV-1.

Each patch of Examples 21 and 22 and Comparative Examples 10 and 11 was stored in a dry condition at 40° C., and the weight of each patch was measured with time and converted to the decreased amount of water to obtain the change of the water content in the pasty preparation. The results are shown in FIG. 6. In the Figure, the initial water content is set to 100%, and the water content is shown in % of the initial value.

Test Example IV-2. Adhesive Power Test of Patch

Regarding each patch of Examples 21 and 22 and Comparative Examples 10 and 11, the adhesive power was measured according to the method described in Japanese Industrial Standards (JIS) Z0237. Also, each aqueous patch was stored in a dry condition at 40° C., and the change of the adhesive power was measured with time. The test results are shown in Table 10. The adhesive power in the Table is shown in the weight (g) of a steel ball which stopped on the pasty preparation surface. Furthermore, the value in parentheses is the water content in the pasty preparation of each formulation after dried for 4 hours at 40° C. (% of the initial value).

TABLE 10

| Drying time | 0 hr | 2 hr | 4 hr | 6 hr | 8 hr |
|---|---|---|---|---|---|
| Ex. 21 (71.0%) | 150 g | 111 g | 111 g | 95 g | 95 g |
| Ex. 22 (80.8%) | 253 g | 253 g | 253 g | 253 g | 253 g |
| Comp. 10 (19.6%) | 111 g | 16 g | 16 g | 13 g | 13 g |
| Comp. 11 (26.5%) | 224 g | 224 g | 224 g | 111 g | 111 g |

Figure 7:
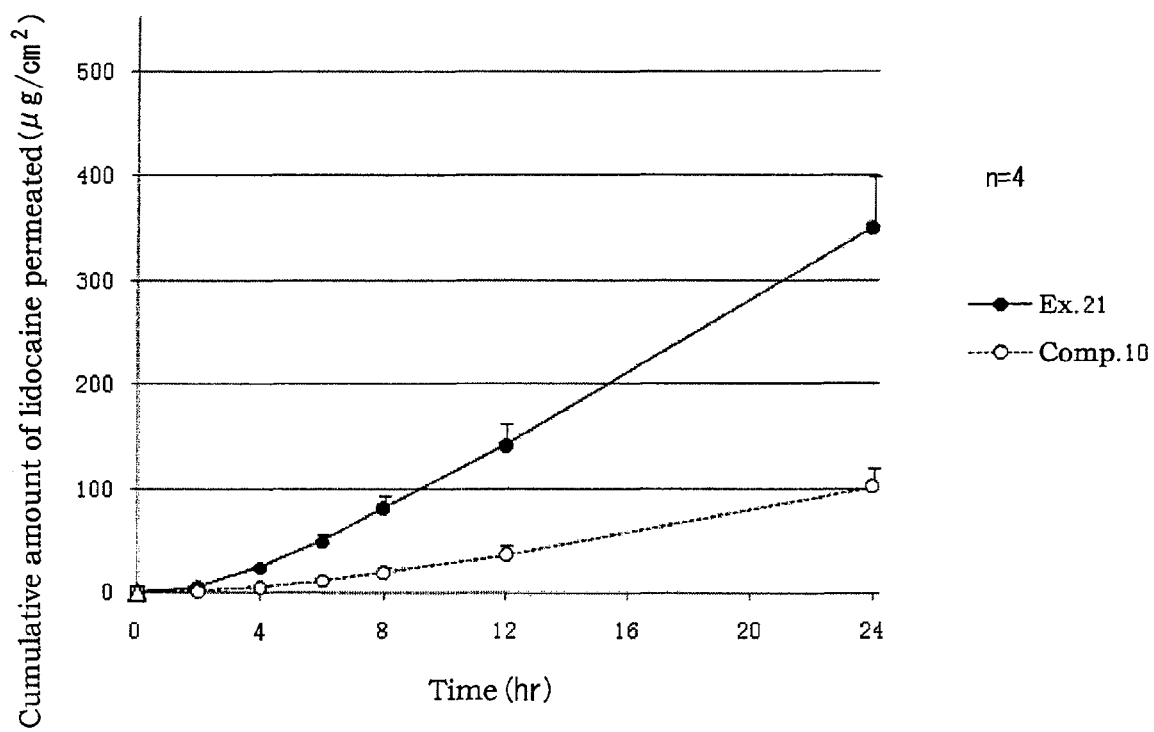
FIG. 7 shows the result of in vitro skin permeability test of each formulation of Test Example IV-3A.

Test Example IV-3A. Excised Skin Permeability Test of Lidocaine-Containing Patch Each patch of Example 21 and Comparative Example 10 was punched into a round shape of 14 mm in diameter, subjected to the same test as Test Example II-3, and the lidocaine-release property from each formulation was investigated. The results are shown in FIG. 7.

Figure 8:
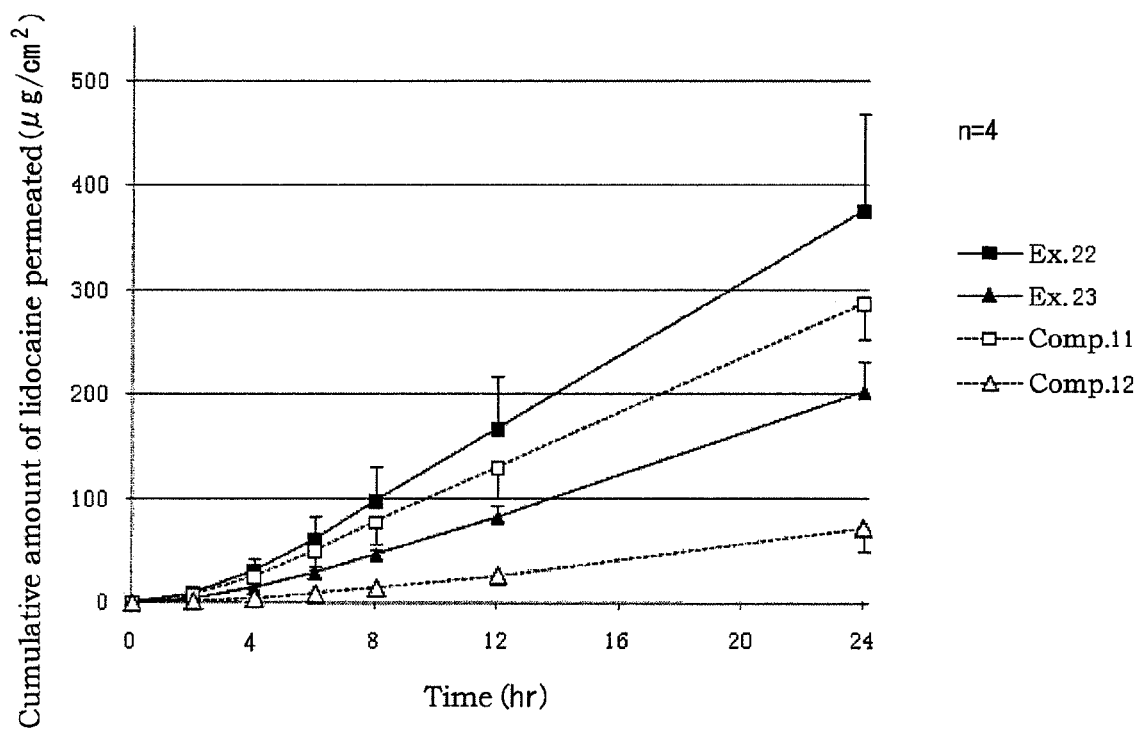
FIG. 8 shows the result of in vitro skin permeability test of each formulation of Test Example IV-3B.

Test Example IV-3B. Excised Skin Permeability Test of Lidocaine-Containing Patch Each patch of Examples 22 and 23 and Comparative Examples 11 and 12 was punched into a round shape of 14 mm in diameter, subjected to the same test as Test Example II-3, and the lidocaine-release property from each formulation was investigated. The results are shown in FIG. 8.

Figure 9:
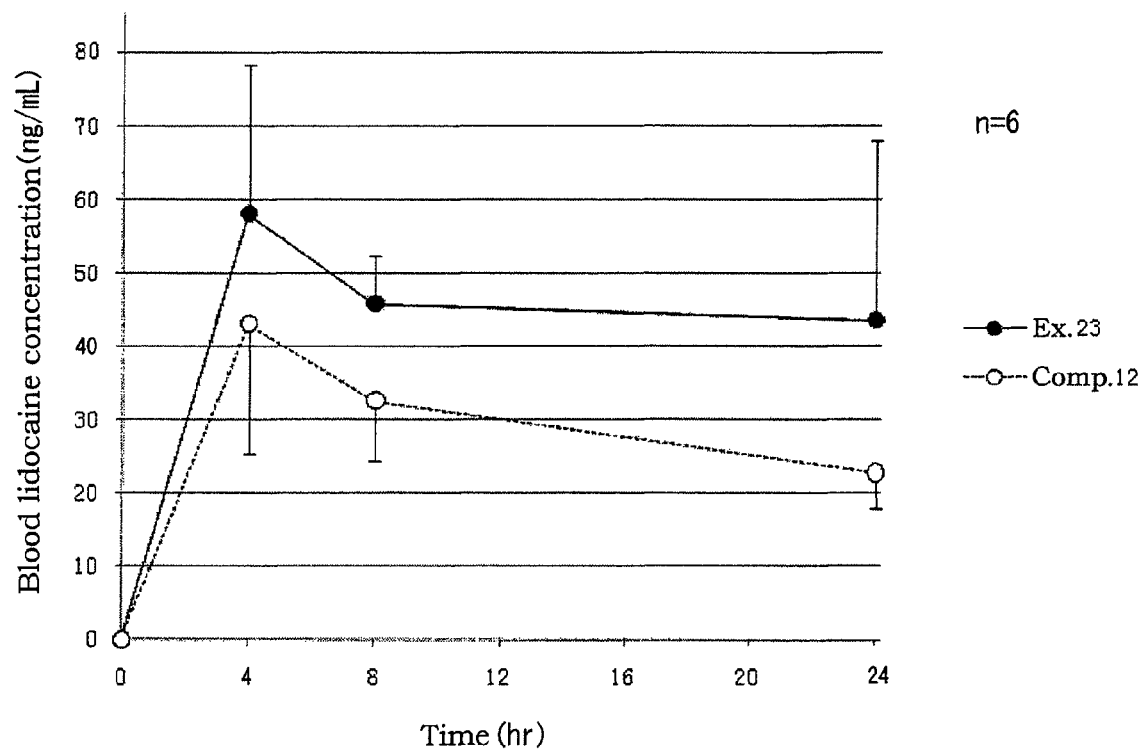
FIG. 9 shows the result of rat blood concentration measurement of each formulation of Test Example IV-4.

Test Example IV-4. Blood Lidocaine Concentration about Lidocaine-Containing Patch Each patch of Example 23 and Comparative Example 12 was punched into the size of 2 cm×3 cm to obtain the test formulation. Each test formulation was applied to a hairless rat's back, then the blood was collected from the rat with time, and the amount of lidocaine in the collected blood was measured. The results are shown in FIG. 9.

[Discussion]
i) Adhesiveness

As shown in Table 10, the patches of Examples were more excellent in adhesiveness than the patches of Comparative Examples in all pasty preparation thicknesses. After dried for 8 hours at 40° C., while the formulations of Comparative Examples showed rapid decreases in adhesive power, the formulations of Examples showed almost no decrease in adhesive power. Therefore, the effect of the backings used in Examples on the adhesion stability of the pasty preparation was demonstrated. Especially, it was also found that said effect became more significant in the formulation having the pasty preparation thickness of 500 g/m².

ii) Drug-Release Property

As shown in FIGS. 7 and 8, the formulations of Examples showed more excellent lidocaine-release properties than the formulations of Comparative Examples. Especially, when the patch of Example was compared to the patch of Comparative Example having the same pasty preparation thickness (cumulative amount of drug permeated after 24 hours from the start of the test about the patch of Example/cumulative amount of drug permeated after 24 hours from the start of the test about the patch of Comparative Example), while the comparison between the thin formulations (500 g/m²) showed the 3.4 times higher drug-release property and the comparison between the thinner formulations (300 g/m²) showed the 2.8 times higher drug-release property, the comparison between the thick formulations (1000 g/m²) showed the 1.3 times higher drug-release property in the patch of Example than the patch of Comparative Example. Therefore, the effect of the patch of the present invention became more significant in the thin formulation.

Also, as shown in FIG. 9, during the later stage of the application, while the blood drug concentration about the formulation of Example 23 was maintained, the blood drug concentration about the formulation of Comparative Example 12 decreased. Therefore, the formulation of Example was also proved to be the formulation having the longer-term persistence of drug efficacy.

As shown in the results described above, it was confirmed that because of its ability to definitely control the water evaporation by the backing regardless of the pasty preparation composition, the patch of the present invention was excellent in adhesive power and adhesion stability, and further, excellent in drug-release property and persistence of drug efficacy when a drug was contained in the pasty preparation.

INDUSTRIAL APPLICABILITY

An aqueous patch having a backing of a three-layer structure of the present invention, wherein the backing consists of an inner fiber layer for holding a pasty preparation, a film layer having through-holes for controlling the water evaporation, and an air-permeable outer fiber layer which prevents exuding out of the pasty preparation or a liquid component exuded from the pasty preparation and a water-containing pasty preparation is spread between the inner fiber layer side and a liner, is able to appropriately adjust the water evaporation from the pasty preparation, excellent in adhesive power and shape retention ability, and very useful as a patch which can be applied for a long time. Also, when a drug is contained in the pasty preparation, the patch is also excellent in drug-release property and persistence of drug efficacy.

The invention claimed is:

1. An aqueous patch having a backing consisting of three layers,
    wherein a film layer having through-holes is laminated between an inner fiber layer and an air-permeable outer fiber layer,
    wherein a pasty preparation is spread on the inner fiber layer side of the backing,
    wherein the inner fiber layer contains through-holes and the film layer is an olefin elastomer,
    wherein the outer fiber layer does not contain through-holes,
    wherein the through-holes have an opening area of 1-18 $mm^2$ per 1 $cm^2$ of the film layer,
    wherein the through-hole area per hole is 0.01-0.8 $mm^2$, and
    wherein the through-holes are filled with the pasty preparation.

2. The aqueous patch according to claim 1, wherein the backing has a moisture permeability of 1000-5000 $g/m^2 \cdot 24$ h.

3. The aqueous patch according to claim 1, wherein the film layer of the backing is perforated so that 30-90% of the water content in the pasty preparation can remain after incubation at 40° C. for 4 hours.

4. The aqueous patch according to claim 1, wherein the pasty preparation contains a drug.

5. The aqueous patch according to claim 4, wherein the drug in the pasty preparation contains a nonsteroidal antiphlogistic or a local anesthetic.

6. The aqueous patch according to claim 4, wherein the drug in the pasty preparation contains ketoprofen or felbinac.

7. The aqueous patch according to claim 4, wherein the drug in the pasty preparation contains lidocaine.

* * * * *